US011437134B2

(12) United States Patent
Southam

(10) Patent No.: US 11,437,134 B2
(45) Date of Patent: Sep. 6, 2022

(54) RECOMMENDING CONSUMER PRODUCTS USING PRODUCT-INGREDIENT EFFICACY AND/OR USER-PROFILE DATA

(71) Applicant: iFormulary, LLC, Minneapolis, MN (US)

(72) Inventor: Adam Gyles Southam, Minneapolis, MN (US)

(73) Assignee: MyFormulary LLC, Minneapolis, MN (US)

( * ) Notice: Subject to any disclaimer, the term of this patent is extended or adjusted under 35 U.S.C. 154(b) by 0 days.

(21) Appl. No.: 14/347,599

(22) PCT Filed: Sep. 27, 2012

(86) PCT No.: PCT/US2012/057678
§ 371 (c)(1),
(2) Date: Mar. 26, 2014

(87) PCT Pub. No.: WO2013/049427
PCT Pub. Date: Apr. 4, 2013

(65) Prior Publication Data
US 2014/0236622 A1 Aug. 21, 2014

Related U.S. Application Data

(60) Provisional application No. 61/539,486, filed on Sep. 27, 2011.

(51) Int. Cl.
*G16H 20/60* (2018.01)
*G06Q 10/04* (2012.01)
(Continued)

(52) U.S. Cl.
CPC ............ *G16H 20/60* (2018.01); *G06Q 10/04* (2013.01); *G06Q 30/02* (2013.01); *G16H 20/30* (2018.01)

(58) Field of Classification Search
CPC ........ G16H 20/60; G16H 20/30; G06Q 10/04; G06Q 30/02; G06Q 30/0601; G06Q 50/10
See application file for complete search history.

(56) References Cited

U.S. PATENT DOCUMENTS

2004/0001874 A1* 1/2004 Davidson ................ A23L 33/12
424/439
2010/0262556 A1* 10/2010 Shaya ..................... G06Q 30/02
705/347

FOREIGN PATENT DOCUMENTS

JP   2008097231 A  *  4/2008

OTHER PUBLICATIONS

Luo, Gang. "Navigation Interface for Recommending Home Medical Products." Original Paper. Received: Mar. 25, 2010 / Accepted: May 31, 2010 / Published online: Jun. 9, 2010. (Year: 2010).*

(Continued)

*Primary Examiner* — Linh Giang Le
(74) *Attorney, Agent, or Firm* — Fantastic IP Consulting; Eduardo E. Drake

(57) ABSTRACT

To help consumers around the world reduce the confusion and complexity of choosing among thousands of wellness products that are effective for their particular medical conditions and/or wellness goals, the present inventor, devised one or more exemplary systems, methods, software, and data structures for recommending products, such as health, fitness, and nutritional products, to consumers. One exemplary system receives user profile information, such as gender, age, medical condition(s), wellness goal(s), biometric data, allergies and sensitivities, and/or nutrition information, and recommends products based on the consumer profiles and product ingredient efficacy and/or contraindications for the medical conditions and/or wellness goals. The system recommends the most scientifically effective (Continued)

products for a particular consumer, while accounting for contraindications thereby reducing risk potentially harmful products. The system ultimately empowers consumers around the world to make safer and more knowledgeable decisions regarding their own wellness.

12 Claims, 13 Drawing Sheets

(51) Int. Cl.
  *G06Q 30/02*   (2012.01)
  *G16H 20/30*   (2018.01)

(56) References Cited

OTHER PUBLICATIONS

PCT/US2012/057678, International Search Report dated Jul. 3, 2014, 5 pages.

\* cited by examiner

| Registration | Gender | Age | Achieve | Prevent & Treat | Diets & Filters | Allergies | Biometrics | Nutrition | Medical Questionnaire | Rx |

Step 8 of 11 — Complete as many steps as you can. Your work is saved automatically.

360

Your Biometric Data (Please Fill All Known):

1 RM Chest Press [____]

Activity Level
- ○ None
- ○ 60 min, high intensity, most days
- ○ 60 min, high intensity, 3-5 days/week
- ○ 30 min, moderate, most days
- ○ 20-30 min, moderate, 3-5 days/week
- ○ 10-20 min, light, 1-2 days/week
- ○ sedentary Aerobic Test [____]

Blood Pressure
(Systolic/Diastolic)
- ○ None
- ○ 110 / 60 - 80
- ○ 110 / 80 - 90
- ○ 110 / 90 +

Body Fat % [____]

Body Weight [____]

Cholesterol [____]

Cholesterol [(Please Choose) ▼]

HDL [____]

LDL [____]

Oxygen Consumption (Vo2) [____]

[Back] [Save & Exit]

FIG. 3F

| Registration | Gender | Age | Achieve | Prevent & Treat | Diets & Filters | Allergies | Biometrics | Nutrition | Medical Questionnaire | Rx |

Step 10 of 11 — Complete as many steps as you can. Your work is saved automatically.

Critical Health:

- ☐ I am currently being treated for a medical condition
- ☐ I am currently on a special diet (vegetarian, low-fat, low sodium, gluten free)
- ☐ I am currently taking prescription medications
- ☐ I am currently taking vitamins and/or supplements
- ☐ Has your doctor ever said that you have a heart condition and that you should only do physical activity recommended by a doctor?

Have you ever been denied life insurance?
○ yes
○ no

Have you ever been hospitalized?
○ yes
○ no

Have you ever been treated for a nervous condition?
○ yes
○ no

Have you ever had surgery or been advised to do so?

[Back] [Save & Continue] [Save & Exit]

Vitamins & Minerals  Supplements  Diet  Protein  Energy  Sports  Nutrition  Grocery  Wines  Beauty  Baby  Children  Sleep  Medicines  See More

TAKE CHARGE OF YOUR HEALTH Personalize your site to your goals & conditions

Home > My Products

High blood pressure

Result pages: 1  2  3  4  5  6  7  8  9  10  ...  298  △

-- Product

Learn more

SCIENTIFIC EVIDENCE GRADES
- [A] Strong Positive
- [B] Positive
- [C] Unclear
- [D] Negative
- [F] Strong Negative

391

High blood pressure (A1B1C1)
- Calcium ([B])
- Soy (Glycine max) ([C])
- Magnesium ([A])

☆☆☆☆☆
0 of 5 (0 reviews)

397

392

393

TwinLab
Daily Two Caps Without Iron
Total Score: [A]1[B]1[C]1 (why?)
Ingredients    391A
☆☆☆☆☆
0 of 5 (0 reviews)

Schiff
Super Calcium 1200
Total Score: [A]1[B]1 (why?)
Ingredients
☆☆☆☆☆
0 of 5 (0 reviews)

RECOMMENDING CONSUMER PRODUCTS USING PRODUCT-INGREDIENT EFFICACY AND/OR USER-PROFILE DATA

RELATED APPLICATION

The present application claims priority to U.S. Provisional Patent Application Ser. No. 61/539,486, which was filed Sep. 27, 2011. This application is incorporated herein by reference.

COPYRIGHT NOTICE AND PERMISSION

A portion of this patent document contains material subject to copyright protection. The copyright owner has no objection to the facsimile reproduction by anyone of the patent document or the patent disclosure, as it appears in the Patent and Trademark Office patent files or records, but otherwise reserves all copyrights whatsoever. The following notice applies to this document: Copyright © 2011, Adam Gyles Southam.

TECHNICAL FIELD

Various embodiments of the invention concern online electronic commerce (ecommerce) and product-recommendation systems, particularly such systems in the health, fitness, food, vitamin, mineral, supplement and nutrition industries.

BACKGROUND

Global interest in health, fitness, and nutrition, and more generally wellness, has exploded in recent years. Mirroring this explosion in interest are the numbers of vitamin, mineral, health, and nutritional supplements as well as food and skin care products available for purchase on and offline, through retailers, such as GNC, Vitamin Shoppe, Vitamin World, Walgreens, Whole Foods, and Trader Joe's.

One problem the present inventor has recognized is that consumers of vitamins, minerals, and health supplements (VMHS) and food and skin care products are barraged with conflicting claims of purity, quality, and efficacy for these products. Even if all the claims were completely accurate, consumers would still find it challenging to select products that meet their exact needs. Indeed, many products that are considered "good" for one consumer need, such as weight loss, may be "bad" for another need, such as immune system enhancement. Moreover, consumers may fail to take account of existing medical conditions or propensities, such as high blood pressure, that would suggest avoidance of certain supplements or products.

This problem has yet to be effectively addressed by retailers, by health and fitness practitioners, pharmacists, and physicians, or by Internet search engines. Retailers, such as GNC, Vitamin Shoppe, Vitamin World, Walgreens, Whole Foods, Trader Joe's, generally lack personnel with sufficient knowledge to make legitimate or effective product recommendations for the treatment or prevention of medical conditions and/or the pursuit of health, wellness, aesthetic or wellness goals. The problem is compounded in situations where multiple medical conditions or wellness goals are involved, and even more so where contraindications amongst supplements and between foods, prescription pharmaceuticals and over-the-counter remedies are accounted for.

Physicians and pharmacists, even when equipped with the knowledge to make such product recommendations, are not readily accessible to consumers and/or do not have the time or financial incentive to provide detailed counseling, leaving consumers to fend for themselves. Fitness professionals seldom have complete information, and even if they do, typically lack efficient mechanisms for delivering their recommendations in a scalable and financially viable way and/or effective ways of managing the liability of making errant recommendations.

The Internet is a great resource for product information and even some expert recommendations. However, the information is not only highly dispersed or fragmented, but also provided by product marketers or those with financial interest in particular product sales, raising questions of accuracy and credibility. Moreover, generic search engines, such as Google and Bing, may help prioritize information based on relevancy and/or popularity, but do little to nothing to help consumers manage the risks of using multiple products for multiple goals and/or conditions.

Accordingly, the present inventor has identified a need to help consumers around the world identify and purchase wellness products that are effective for their particular medical conditions and/or wellness goals.

SUMMARY

To address this and/or other needs, the present inventor, devised one or more exemplary systems, methods, software (machine-readable and executable instructions), and data structures for recommending products, such as health, fitness, and nutritional products, to consumers. For example, one exemplary ecommerce system receives user profile information, such as gender, age, medical condition(s), wellness goal(s), biometric data, allergies and sensitivities, and/or nutrition information, and recommends products based on the consumer profiles and product ingredient efficacy and/or contraindications for medical conditions and/or wellness goals. The systems provide recommendations for the most effective products for a particular consumer, while reducing the risk of consumers buying ineffective or potentially harmful products.

Notably, the exemplary system can be deployed across a health, wellness, fitness, and/or sports club system, with revenue from member purchases of recommended products through an ecommerce site associated with their respective clubs. In addition, club members earn loyalty rewards or points for purchases made through the system. In some instances, the loyalty rewards or points can be used to offset club membership fees or to purchase other club services and/or products. The exemplary system can also be used by clients of personal trainers, massage therapists, healthcare providers, physicians, pharmacists, nutritionists, health maintenance organizations, insurance companies and/or hospitals who share revenue from client purchases with the owner of the ecommerce site and who can also provide loyalty rewards for these purchases.

The exemplary system promises to set a new standard for rigor and thoroughness for matching products with the specific needs of the consumer. The system's ability to scan through multiple proprietary and public databases of product ingredient efficacy such as the Natural Medicine Quality Standard, U.S. National Library of Medicine or the National Center for Biotechnology Information provides confidence in recommending vitamins, minerals, supplements, food and skin products. The process helps guide consumers in making good decisions as this system grades the effectiveness of vitamins, minerals, supplements, herbs and foods for various ages, genders, health, wellness, aesthetic and wellness goals and medical conditions. The system's grading system is objective and reliable, empowering consumers around the world to make safer and more knowledgeable decisions regarding their own wellness.

BRIEF DESCRIPTION OF DRAWINGS

This document includes a set of accompanying figures FIGS. 1-5, which depict various systems, components, process blocks, and/or other elements, aspects, or features that are annotated with reference numbers. In these figures like reference numerals refer to identical or functionally similar elements throughout the separate views.

More particularly.

FIGS. 3A-3I are screenshots of exemplary graphical user interfaces which correspond to one or more embodiments of the present invention.

Figure 1:
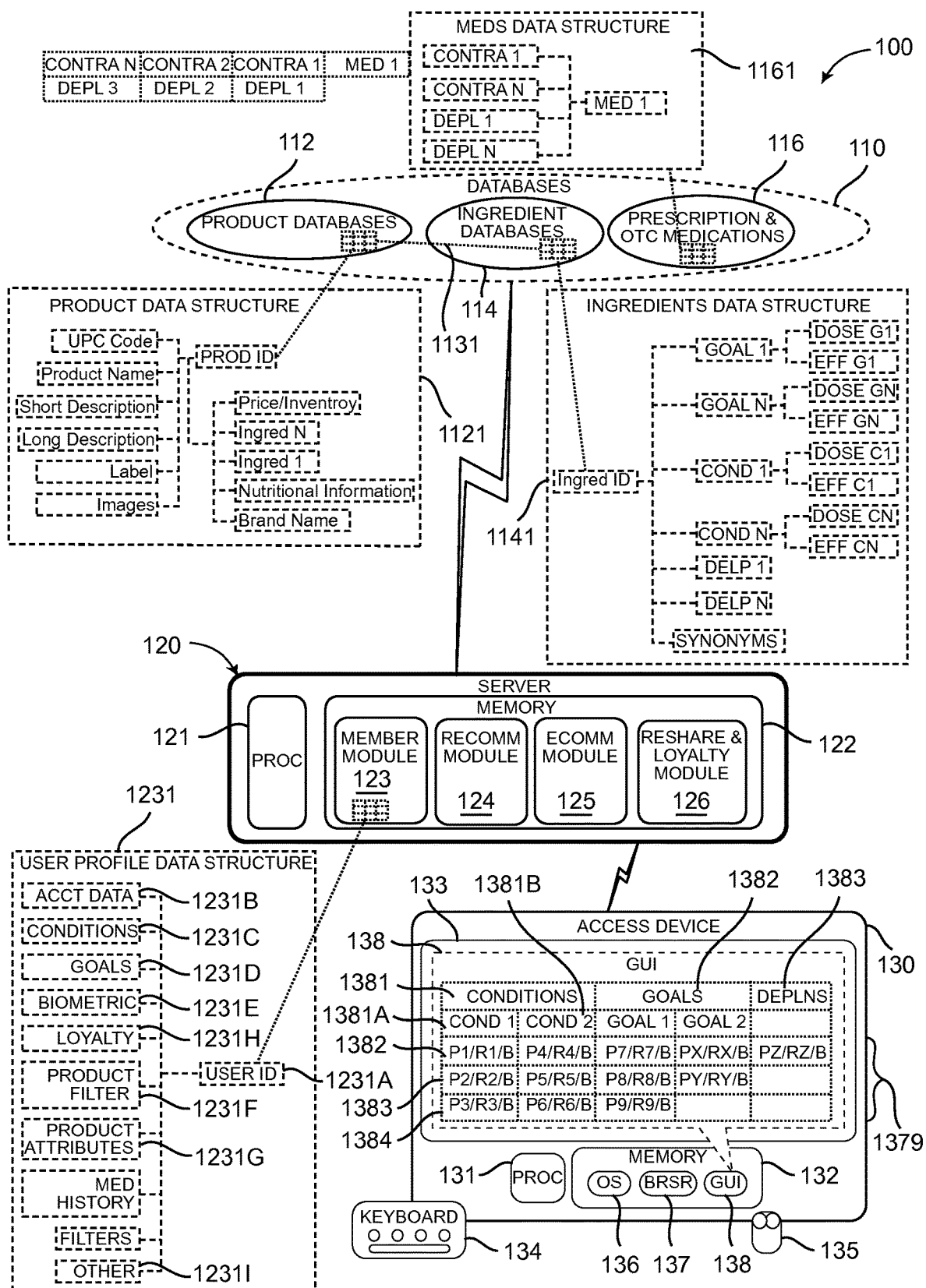
FIG. 1 is a block diagram of an exemplary online ecommerce and product recommendation system which corresponds to one or more embodiments of the present invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EXEMPLARY EMBODIMENT(S)

This document, which incorporates the drawings and the appended claims, describes one or more specific embodiments of an invention. These embodiments, offered not to limit but only to exemplify and teach the invention, are shown and described in sufficient detail to enable those skilled in the art to implement or practice the invention. Thus, where appropriate to avoid obscuring the invention, the description may omit certain information known to those of skill in the art.

Exemplary Definitions

This description includes many terms with meanings derived from theft usage in the art or from their usage within the context of the description or claim. However, as a further aid, the following exemplary definitions are presented.

The vitamin, mineral, and health supplement (VMHS) category includes "alphabet" vitamins multi-vitamins, aromatherapy, herbal extracts, and macrobiotic, homeopathic, herbal and botanical remedies.

Sports nutrition products include protein and weight gain supplements, sports drinks and bars, and high-potency vitamins.

Weight loss products include diet pills, shakes, bars, teas, meal replacements; and low-carb items. Foods include beans, fruits, herbs, legumes, natural sweeteners, nuts, oils, seeds, vegetables, acai, bee products, greens, resveratrol and more. Skin Care Products include bath salts and oils, shampoos, conditioners, lotions, creams, soaps, scrubs, teeth cleaners and whiteners, ointments, elixirs, analgesics, antibiotics, vitamins and minerals.

Herein, the term "wellness product" includes any human-ingestible or topically applied product including all of the above items and any vitamin, mineral, supplement, herb, spice, elixir, plant, vegetable, animal, fish or chemical compound.

Fitness Clubs include wellness clubs, health clubs, sports clubs, university organization, sports teams, health maintenance organization, sports association or member organization.

Herein, the term "consumer" is used interchangeable with the terms "member", "purchaser", "buyer", or "user" of the goods, services, or content that a solution has to offer.

Herein, the term "club" is interchangeable with the words "organization", "practice", "association" or "team" and any synonyms to these terms in existence now or in the future in any language Herein, the term "wellness goal" or "goal" is interchangeable with the term "wellness goal", "wellness goal", "health goal", "athletic goal", "aesthetic goal", "dietary goal", or "beauty goal" and any synonyms to these terms in existence now or in the future in any language.

Herein, the term "medical condition" or "condition" is interchangeable with the term "medical condition", "physical condition", "health condition", "condition requiring prescription or over-the-counter medication", "bodily condition", "disease", "ailment", "illness", "disability", "disorder", "morbidity", "syndrome", "predisease", or "medicalization" and any synonyms to these terms in existence now or in the future in any language.

Moreover, the terms "a" and "an" refer to at least one. As used herein, the term "or" is used in its Boolean logical sense, unless used in conjunction with "either." Relational terms, such as second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended as open ended or non-exclusionary terms, such that a process, method, article, system, apparatus, device, medium, or structure that comprises, has, includes, contains a list of elements does not include only those elements but may include other elements not expressly listed or inherent to such process, method, article, or apparatus. An element proceeded by "comprises a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" or "arranged" or "adapted" in a certain way is configured, arranged, or adapted in at least that way.

Exemplary System

FIG. 1 shows an exemplary ecommerce and product recommendation system 100, which incorporate the capabilities, functions, methods, interfaces, and so forth describe herein. System 100 includes one or more databases 110, one or more servers 120, and one or more access devices 130.

Exemplary Databases

Databases 110 includes a set of product databases 112, ingredient databases 114, and medication databases 116. Product databases 112, in the exemplary embodiment, include a set of product data structures, of which product data structure 1121 is representative. Data structure 1121 includes a product ID or identifier field or portion, which is logically associated with one or more product-related data fields or objects, such as a UPC Code field, a Product Name field, Short Description field, Long Description field, Label field, Images field, Brand Name field, Nutrition Information field, Ingredient 1 field and Ingredient N field, and a Price-Inventory field, and an Other field.

More precisely, UPC Code field includes Universal Product Code for the product, which in some embodiments may differ from its product ID. Product name field includes text form of the product name; short description field includes a short form description of the product, for example less than 140 characters. Long descriptions field includes a long form description or a pointer to a long form description, for example greater than 140 characters. Label field includes a pointer to or the actual text and/or image of the product label. Images field includes image data or one or more pointers to images associated with the product. Brand name field includes one or more brand names associated with the product.

Nutritional information field includes information regarding the nutritional value of the products, for example in relation to recommended daily allowance of various vitamins, minerals, carbohydrates, proteins, fats, etc. Ingredient fields 1 and N each identify, list, point to, or otherwise indicate or represent a corresponding ingredient in the associated product. In some embodiments, two or more ingredients may be combined and treated as a single ingredient. Also some embodiments include the ingredient identify information in association with an ingredient quantity indicator, for example as a percentage of the given ingredient within a serving size of the product or relative to other active ingredients in the products. Price-Inventory field includes price-related data for the associated product, such as single or multi-unit sales price and profit margin or other price-related business rules. It also includes, in some embodiments, inventory information, such as an in-stock or out-of-stock flag, a quantity remaining.

Ingredient database 114 include ingredient data and associated efficacy information extracted from sources such as the Natural Standard. Ingredient database 1141 includes a number of ingredient records or objects, generally data structures, of which ingredient data structure 1141 is representative. Ingredient data structure includes an ingredient ID field or portion which is logically associated with a goal 1 field, a goal n field, a condition 1 field, a condition N field, a depletion 1 field, a depletion 2 field, and synonyms field.

Goal fields 1 and N, each of which identify, indicate, represent, or point to a fitness or health related goal—generally wellness goal, are each associated with a corresponding dose field and an efficacy rating field. Each dose field provides dosing information for the corresponding ingredient for achieving the associated goal, and the efficacy rating field indicates, represents, or points to an efficacy rating and/or rating source for the ingredient relative to the associated goal at the prescribed dose. The exemplary embodiment uses an A, B, C, D or F ratings system as further described below. However, other embodiments may user other efficacy ratings systems.

Conditions fields 1 and N, each of which identify, indicate, represent, or point to a corresponding medical condition, are each logically associated by pointer or arrangement or other means to a corresponding dose field and an efficacy rating field. Each dose field provides dosing information for the corresponding ingredient for preventing or treating the associated medically condition, and the efficacy rating field indicates, represents, or points to an efficacy rating and/or rating source for the ingredient relative to the associated medical condition at the prescribed dose.

Depletion fields 1 and N each identify, indicate, represent, or point to a corresponding depletion, i.e, a substance, eg. vitamin or mineral, which is generally depleted from a user's body as a result of using or ingesting the corresponding ingredient or product. are each logically associated by pointer or arrangement or other means to a corresponding dose field and an efficacy rating field.

Synonyms field identifies, indicates, represents, or points to a one or more terms that are known in the wellness or more generally scientific community to be synonymous, equivalent, or chemically interchangeable with the corresponding ingredient. For example, fish oil is synonymous with ALA, alpha-linolenic acid (ALA, C18:3n-3), cod liver oil, coldwater fish, DHA, docosahexaenoic acid (DHA, C22:6n-3), docosapentaenoic acid (DPA, 22:5n-3), DPA, eicosapentaenoic acid (EPA, C20:5n-3), EPA, fish body oil, fish extract, fish liver oil, fish oil fatty acids, halibut oil, long-chain polyunsaturated fatty acids, Lovaza®, mackerel oil, marine oil, MaxEPA®, menhaden oil, n-3 fatty acids, n-3 polyunsaturated fatty acids, Omacor®, Omegaven®, omega fatty acids, omega-3 fatty acids, omega-3 oils, polyunsaturated fatty acids (PUFA), salmon oil, seal oil, shark liver oil, w-3 fatty acids.

In some embodiments, each ingredient in product data structure 1121 is logically associated with an ingredient data structure, such as data structure 1141, defining a larger data structure logically associating each product to goals, conditions, depletions, efficacy ratings, and doses. Logical association link 1131 is included in the figure to represent this linkage and the resulting larger data structure.

Medications database 116 generally provides contraindication and depletion information for prescription and non-prescription (over-the-counter (OTC)) medications. Database 116 includes a number of medication records or objects, generally data structures, of which medication data structure 1161 is representative. Medication data structure 1161 includes a medication identifier field, which is logically associated with one or more contraindication fields, such contraindication fields 1 and N, with each contraindication field identifying, indicating, representing, or pointing to one or more ingredients, other medications, foods, substances, or products that have been determined to be incompatible with the corresponding medication. The medical identifier field is also logically associated with depletions fields 1 and N. Each depletion field indicates, represents, or points to a substance, eg. vitamin or mineral, which is generally depleted from a user's body as a result of using or ingesting the associated medication.

In some embodiments the information of databases 112, 114, and 116 are organized as a set of tables.

Ingredients List of all known ingredients (master ingredients like beta-glucan have many synonyms—engine runs from master ingredient)

Synonyms Table of all synonyms for master ingredients (eg. see beta-glucan below)

Consumer Information

Conditions Table of all medical conditions

Goals Table of all wellness goals

Efficacy Table of rankings of every master ingredient for every condition and every goal Contraindications Table of every ingredient with contraindications to another ingredient for a specific condition or goal Rx Table of all pharmaceuticals Rx Table of all Rx contraindications with other Rx or master Contraindications ingredient (including synonyms)

Depletions Table of all depletions caused by Rx or ingredient usage

Age Table of ingredients specific to age-related conditions/goals/depletions

Gender Table of ingredients specific to gender-related conditions/goals/depletions Filters Table of ingredients or substances to be filtered from results (eg. sugar, salt, International Olympic Committee banned substances, NCAA banned substances, wheat, pollen, milk products, etc.

Effectors Table of recommendations based upon consumer information input (eg. consumer enters HDL/LDL ratio of 5; ingredients known to lower cholesterol and triglycerides are added to the list (so a person may not check hyperlipidemia in the conditions (treat and prevent) section but by filling out other information in the engine, ingredients get tagged and products containing those ingredients result Allergies Table of allergies Depletions Table of Rx and OTC depletions Databases 110, which take the exemplary form of one or more electronic, magnetic, or optical data-storage devices, include or are otherwise associated with respective indices (not shown). Databases 110 are coupled or couplable via a wireless or wireline communications network, such as a local-, wide-, private-, or virtual-private network, to server 120.

Exemplary Server

Server 120, which is generally representative of one or more servers for serving data in a variety of desirable form, including for example webpages or other markup language forms with associated applets, ActiveX controls, remote-invocation objects, or other related software and data structures to service clients of various "thicknesses." More particularly, server 120 includes a processor module 121, a memory module 122, a subscriber or user database 123, a product recommendation engine or module 124, an ecommerce module 125, and a revenue sharing and-loyalty module 126.

Processor module 121 includes one or more local or distributed processors, controllers, or virtual machines. In the exemplary embodiment, processor module 121 assumes any convenient or desirable form.

Memory module 122, which takes the exemplary form of one or more electronic, magnetic, or optical data-storage devices, stores user database 123, product recommendation module 124, ecommerce module 125, and revenue-sharing-and-loyalty module 126.

User module or database 123 includes user-related data and related machine-executable instruction sets for controlling, administering, and managing the user access and data acquisition and storage as described herein. In the exemplary embodiment, user database 123 includes one or more user related data structures, of which data structure 1231 is representative. Data structure 1231 includes a customer or user identifier portion 1231A, which is logically associated with one or more data fields or objects 1231B-I.

\*\*\*Table of all inputted information including age, gender, conditions (prevent and/or treat), goals (achieve), biometrics, nutrition, medical questions, Rx, filters\*\*\*

Field 1231B includes account related data items, such as user name, password, name, address, shipping address, credit card information, age, date of birth, and gender. Field 1231C includes one or more medical conditions as described herein and/or access credentials and permissions for electronic medical records. Field 1231D includes one or more user selected or identified wellness goals as further described herein. Field 1231E includes biometric data regarding the user as described herein and/or access credentials and permissions for electronic physical activity or health monitoring devices, services or systems, for example, electronic pedometers and/or networked fitness equipment. Field 1231F includes one or more product filter ingredients, for example user allergens, sugar, corn, wheat, soy, or their derivatives, that the associated user wants to exclude from any products he or she purchases. Field 1231G includes or identifies one or more product attributes, such as organic, fair trade, or made in the USA, that the associated user has a preference for. (If two or more products are otherwise equal in efficacy and meet all other preference criteria, some embodiments use this attribute as a tiebreaker in system ranking.)

Field 1231H includes one or more loyalty related data items or information for the associated user, such as whether or not they opted into a loyalty system, information identifying the participating fitness club, health care provider, personal trainer, or massage therapist. Additionally, this field includes one or more quantitative scoring fields to indicate cumulative loyalty points the associated user has earned through purchases via the system. In some embodiments, the user may earn loyalty points for participating in health workshops, degrees of completeness of information in the user profile, frequency of updates of the user profile, positive biometric changes, participation in studies, compliance with recommended product consumption or for meeting threshold attendance goals at his or her fitness club. These points may be aggregated with the purchase related loyalty points or maintained in a separate cumulative field.

Field 1231I includes one or more other user related data items that may be described herein, but for which as separate data field has not been enumerated. In some embodiments, data structure 1231 also logically associates purchase history information indicating the products purchased by the user, dates of purchase, purchase price, etc. Additionally, some embodiments include results of user privacy selections, indicating for example whether the user authorizes the system to access its cookie file or similar information to determine what fitness or health products he or she may have viewed and/or purchased on other ecommerce systems, or authorization to share profile information, recommendations or purchase history with medical practitioner(s) of the user's choosing.

Recommendation engine or module 124 includes one or more sets of machine-readable and/or executable instructions for accessing databases 110 and user database 122 to recommend products as described herein. In the general terms, the exemplary recommendation engine receives a set of user profile information, such as one or more medical conditions and/or fitness or wellness goals, and identifies and ranks products having ingredients scientifically demonstrated as being effective in treating or preventing the one or more medical conditions and/or promoting attainment of the one or more wellness goals. The products are then ranked more products graded A through F according to descending efficacy of the ingredients in the products. The data used by the recommendations engine is derived from medical evidence from millions of published scientific reports and clinical studies.

Product efficacy in the exemplary system is rated and presented using a descending set of efficacy grades A, B, C, D, F or X, which are defined respectively as follows:

A. Strong Scientific Evidence: Statistically significant evidence of benefit from >2 properly randomized trials (RCTs), OR evidence from one properly conducted RCT AND one properly conducted meta-analysis, OR evidence from multiple RCTs with a dear majority of the properly conducted trials showing statistically significant evidence of benefit AND with supporting evidence in basic science, animal studies, or theory.

B. Good Scientific Evidence: Statistically significant evidence of benefit from 1-2 properly randomized trials, OR evidence of benefit from >1 properly conducted meta-analysis OR evidence of benefit from >1 cohort/case-control/non-randomized trials AND with supporting evidence in basic science, animal studies, or theory. This grade applies to situations in which a well designed randomized controlled trial reports negative results but stands in contrast to the positive efficacy results of multiple other less well designed trials or a well designed meta-analysis, while awaiting confirmatory evidence from an additional well designed randomized controlled trial.

C. Unclear or Conflicting Scientific Evidence: Evidence of benefit from >1 small RCT(s) without adequate size, power, statistical significance, or quality of design by objective criteria, * OR conflicting evidence from multiple RCTs without a clear majority of the properly conducted trials showing evidence of benefit or ineffectiveness, OR evidence of benefit from >1 cohort/case-control/non-randomized trials AND without supporting evidence in basic science, animal studies, or theory, OR evidence of efficacy only from basic science, animal studies, or theory.

D. Fair Negative Scientific Evidence: Statistically significant negative evidence (i.e., lack of evidence of benefit) from cohort/case-control/non-randomized trials, AND evidence in basic science, animal studies, or theory suggesting a lack of benefit. This grade also applies to situations in which >1 well designed randomized controlled trial reports negative results, notwithstanding the existence of positive efficacy results reported from other less well designed trials or a meta-analysis. (Note: if there is >1 negative randomized controlled trials that are well designed and highly compelling, this will result in a grade of "F" notwithstanding positive results from other less well designed studies.)

F. Strong Negative Scientific Evidence: Statistically significant negative evidence (i.e., lack of evidence of benefit) from >1 properly randomized adequately powered trial(s) of high-quality design by objective criteria. *

X. Unable to evaluate efficacy due to lack of adequate available human data.

Other rating systems and definitions may be utilized by the exemplary system

The exemplary system does not recommend products with a D, F or X rating for treatment or prevention of a medical condition or for attainment of a wellness goal. More precisely, if a product contains an single ingredient rated a D, F, or X in relation to a medical condition or user wellness goal, the exemplary embodiment excludes it automatically from further consideration in its recommendation process. Some embodiments use other types of ratings systems. For example some embodiments use three, four, or five-star rating systems; others use trinary system (thumbs up, thumbs down, don't know or green, yellow, red). Products are then ranked based on the number and efficacy of ingredients that they contain and subsequently filtered based on contraindications and/or interactions with user medications, existing medical conditions, and as well as dietary and allergy information, before being presented to the user as a product recommendation and/or for potential purchase.

Ecommerce module 125 includes one or more sets of machine-readable and/or executable instructions for receiving and processing ecommerce data and effecting financial, shipping, and inventory management functions. In the exemplary embodiment, this entails providing electronic shopping carts, processing credit card payments, initiating shipping orders, and updating inventory management systems.

Revenue sharing and loyalty module 126 includes machine readable and/or executable instruction sets, responsive to purchases, for sharing payments with fitness clubs, personal trainers, massage therapists, and/or healthcare providers according to Reshare® Collaborative Channel Commerce® management arrangement or agreements (U.S. Pat. No. 6,594,641 is incorporated herein by reference.) Additionally, module 126 also includes instructions sets for implementing a loyalty reward program based on user purchases and/or activity as described herein which may be initiated and authorized over a wireless or wireline communications network by users operating one or more accesses devices, such as access device 130.

Exemplary Access Device

Access device 130 is generally representative of one or more access devices. In the exemplary embodiment, access device 130 takes the form of a personal computer, workstation, personal digital assistant, mobile telephone, kiosk, or any other device capable of providing an effective user interface with a server or database. Specifically, access device 130 includes a processor module 131, a memory 132, a display 133, a keyboard 134, touch screen and a graphical pointer or selector 135.

Processor module 131 includes one or more processors, processing circuits, or controllers. In the exemplary embodiment, processor module 131 takes any convenient or desirable form. Coupled to processor module 131 is memory 132.

Memory 132 stores code (machine-readable or executable instructions) for an operating system 136, a browser 137, and a graphical user interface (GUI) 138. In the exemplary embodiment, operating system 136 takes the form of a version of the Microsoft Windows operating system, and browser 137 takes the form of a version of Microsoft Internet Explorer, Firefox, Safari, AOL, Google Chrome, etc. Operating system 136 and browser 137 not only receive inputs from keyboard 134 and selector 135, but also support rendering of GUI 138 on display 133.

Upon rendering, GUI 138 presents data in association with one or more interactive control features (or user-interface elements). (The exemplary embodiment defines one or more portions of interface 138 using applets or other programmatic objects or structures from server 120 to implement the interfaces shown above or elsewhere in this description.) In the exemplary embodiment, each of these control features takes the form of a hyperlink or other browser-compatible command input, and provides access to and control of various regions of the graphical user interfaces described herein.

More particularly, GUI 138 provides in response to the user submitting a request for product recommendations, a results page including three regions, a conditions region 1381, a goals region 1382, and a depletion region 1383, which are shown as simultaneously displayed in the FIG. 1, but which are sequentially displayed in some embodiments. Conditions region 1381 includes medical condition 1 region 1381A and medical condition 2 region 1381B, which a given user has submitted to the system for product recommendations, either directly or by virtue of having associated and a set of ranked user-selectable product identifiers P1, P2, P2 in association with respective efficacy ratings R1, R2, and R3 and corresponding purchase or add-to-cart links B. Ranked product listing 1379, which displays a set of one or more product identifiers 1382, 1383, and 1384 in rank order of efficacy for one or more goals and/or conditions associated with the user.

Exemplary system provides a graphical user interface or voice response and speech recognition system that enables various forms of user interaction and/or navigation through the system, which is preferably a two- or three-tiered system. Exemplary user interactions with the system include at least one or more of the following:

Exemplary Method(s)

Figure 2:
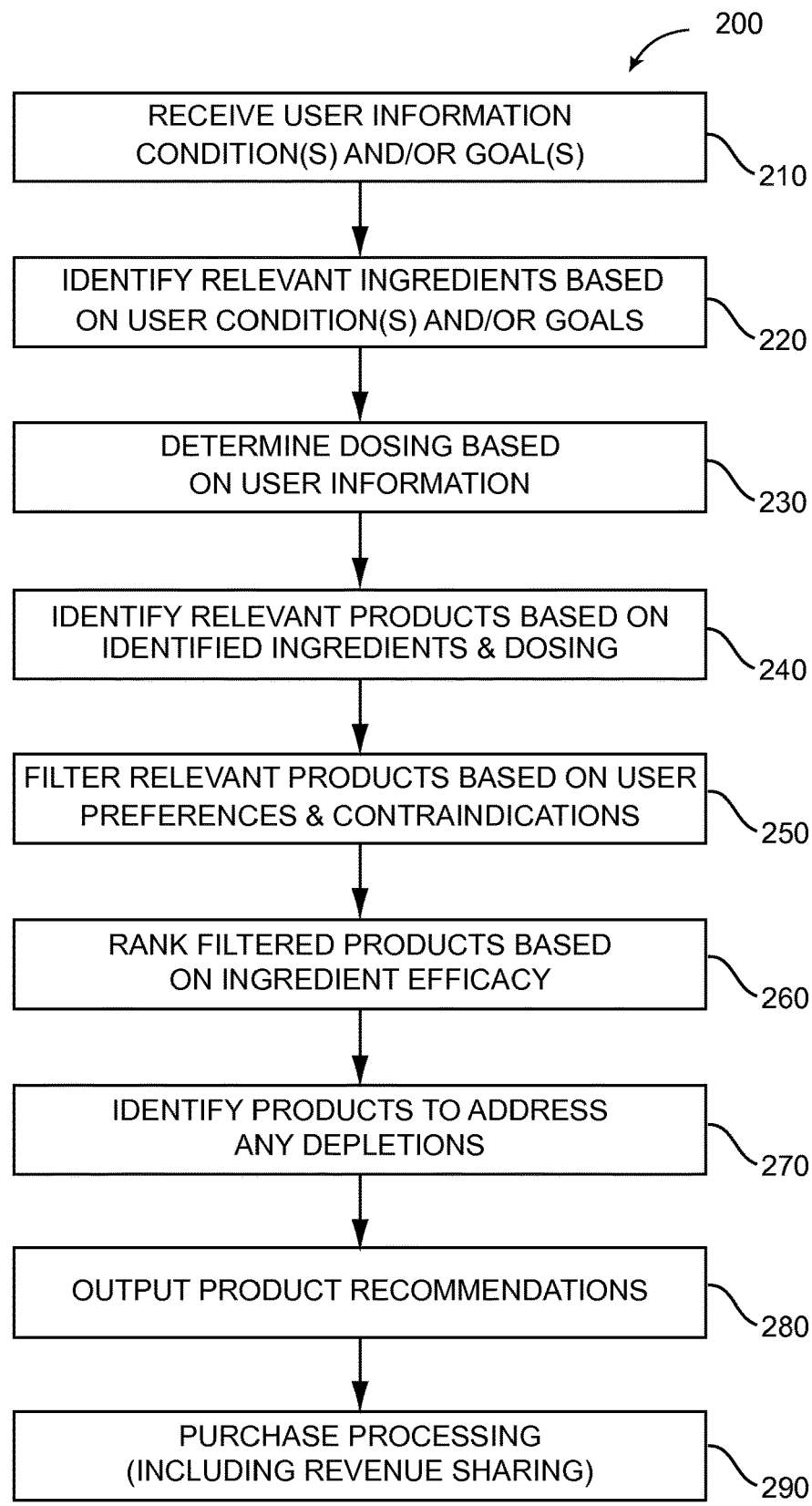
FIG. 2 is flow chart of an exemplary method which corresponds to one or more embodiments of the present invention.

FIG. 2 shows a flow chart 200 of one or more exemplary methods of operating an ecommerce and product recommendation system, such as system 100. Flow chart 200 includes blocks 210-290, which are arranged and described in a serial execution sequence in the exemplary embodiment. However, other embodiments are not similarly limited. Moreover, still other embodiments implement the blocks as two or more interconnected hardware modules with related control and data signals communicated between and through the modules. Thus, the exemplary process flow applies to software, hardware, and firmware implementations.

Block 210 entails the system, specifically server 120, receiving information from or about at least one user. In the exemplary embodiment, the information includes one or more user medical or health conditions and/or one or more user health or wellness goals. In the exemplary embodiment, this entails in one scenario the user accessing a web form or web page or other user interface via an access device, such as access device 130, and either directly entering or selecting one or more medical or health conditions and/or health or wellness goals and then selecting a submit, go, enter or return button that results in transmission of the conditions and/or goals to server 120.

In another scenario, the user is invited to register with the system by inputting name, email address, selecting a user name and password, and then completing one or more portions of a personal profile, which invites the user to provide information regarding his or her gender, age, race, ethnic background, blood type, geographic location, environmental conditions, goals (fitness, lifestyle, wellness, lifestyle, athletic or sports specific) conditions (medical conditions for which the user wants to prevent or treat), biometrics, nutrition, medical history, prescription and non-prescription drug usage, vitamin, mineral, supplement and food usage, allergies, undesirable ingredients (sugar, salt, wheat, banned substances, etc.), and meta-product preferences, such as country of origin, fair trade, etc. (See FIGS. 3A-3H and related description below for details regarding an exemplary tabbed GUI used in the exemplary system to facilitate collection of this and/or other user information.

For example, some embodiments prompt the user to identify or select a health club location where he or she has a membership or alternatively to select a health care provider, physician, athletic organization, massage therapist, herbalist, chiropractor, acupuncturist, yoga instructor, athletic coach, or personal trainer that he or she has a relationship with. The selected or identified entity is then logically associated with the user as part of their profile data. In some embodiments, a set of providers is suggested based on the location or address of the user or an associated Internet Protocol (IP) address. Geographic Information System data, Global Positioning System data, association with organizations, groups or individuals, participation in membership organizations and groups or sub-groups within Facebook, LinkedIN, and the like In some embodiments, the login of a registered user having an existing user profile results in automatic presentation of relevant products based on their existing profile, their past purchases, and includes special offers and promotions for products known to be effective for the most recent conditions and goals associated with the user. Also in some embodiments, one or more user profiles may be automatically updated in response to medical examinations, doctor visits sporting event performance metrics, such race times, automatic biometric reporting systems, and so forth. These updates can used to used to determine whether most recent purchase of supplements or other wellness products are still the best recommended products for a given user to be taking. If a change is warranted, some embodiments will transmit email, text, automated phone calls, and other messages to the user alerting them one or more products are no longer optimal or worse yet threatening. Execution continues at block 220

Block 220 entails identifying a set of product ingredients (or more generally product features, functions or attributes) based on the user information, such as the medical conditions or goals. In the exemplary embodiment, this entails searching a database of medical conditions and wellness goals based on the user inputs, and identifying a set of ingredients clinically proven or otherwise credibly accepted as being effective in promoting treatment or prevention of the medical condition or achievement of the desired wellness goal. More particularly, the exemplary embodiments conducts a separate ingredient search for each user condition and for each goal, maintaining a separate result set for each condition and goal. Ingredients that do not have an efficacy rating of A, B, or C, as determined by the Natural Medicine Quality Standard (Natural Standard), are excluded from search results. (Some embodiments user other efficacy ratings systems and/or other efficacy grading systems.) Execution advances to block 230.

Block 230 entails determining effective dosing (or more generally amounts) of the ingredients based on the user information. In the exemplary embodiment, this entails the system, specifically the recommendation module, using information such as age, weight, blood type, and other biometric markers of the user in combination with stored information regarding recommended daily allowances, minimum effective and maximum allowable amounts and toxicity levels, to compute a recommended dosage for each ingredient. In one embodiment, the recommended dosage is computed as the product of an average dosage amount and the ratio of a user's weight to an average weight used in determining the average dosage If user weight information is unavailable for a particular user, the exemplary system assumes an average dosage amount. Execution continues at block 240.

In block 240, the system identifies a set of one or more relevant products based on the one or more identified ingredients. To this end, the exemplary embodiment searches a product database for products including the identified ingredients or known equivalents for these ingredients in the appropriated dosages. In conducting the search, the exemplary embodiment identifies synonyms for the identified ingredients and conducts the search using the identified ingredients and their synonyms. When the search is concluded, exemplary execution continues at block 250.

Block 250 entails filtering the set of relevant product based on user data, preferences and contraindications amongst any of the ingredients and/or relative to any prescription or over-the-counter medicine or food product the user has provided information about in his or her profile. In the exemplary embodiment, this entails retrieving or referring to a set of user data or preferences or filtering requirements stored as part of or in association with the user's profile. Examples include no or low sugar, no or low salt, no NCAA (National Collegiate Athletic Association) or IOC (International Olympic Committee) banned substances, no wheat, no dairy, and ingredients with specific glycemic index rating. Once the list is retrieved or referenced, any products including ingredients that are designated for filtering are deleted or marked for deletion from the list of relevant products. Also, the exemplary system also eliminates any products containing ingredients that are contraindicated or otherwise incompatible with existing prescription or over-the-counter (OTC) medications, supplements and/or foods that the user has indicated he or she is taking. Execution continues at block 260.

In block 260, the exemplary system ranks the filtered list of relevant products based on efficacy in treating or preventing the medical condition(s) and/or promoting achievement of the one or more health, fitness, wellness or athletic goals. In the exemplary embodiment, this ranking entails determining a weighted score for each product based on the number of effective ingredients it contains and how effective each ingredient is. To this end, the exemplary embodiment totals the number of As, the number of Bs, and Cs ingredients in a product to creates a concatenated character string or score S in the form of $$S_i = AxByCz,$$

Where subscript i denotes product i, x denotes the number of A-rated ingredients in the product l; y denotes the number of B-rated ingredients in product i; and z denotes the number of C-rated ingredients in product i. Thus, for example, a product 1 for weight loss having 3 A-rated ingredients, 2 B-rated ingredients and 0 C-rated ingredients yields a score string of A3B2C0. A second product for weight loss, product 2, may have a score string of A2B5C3, indicating 2 A-rated ingredients, 5 B-rated ingredients, and 3 C-rated ingredients. Once each product is scored in this manner, the exemplary embodiment performs an alphanumeric sort of the scores for the products associated with each condition or goal, thereby determining an efficacy rank for each product. Thus, for example, sorting the respective score strings in ascending order of efficacy yields: A2B5C3 followed by A3B2C0, or in descending order A3B2C0 followed by A2B5C3. In other words, product 1 has a higher efficacy rank for weight loss than product 2.

It is possible that some products or ingredients may be effective for multiple medical conditions or wellness goals. To allow for this and reduce the number of products in play, some embodiments allow user to rank or prioritize their conditions and their goals. In this case, each product can be scored or given a score string for each condition and for each goal and then the separate strings concatenated in the order of prioritization to yield an aggregate score string. For example, a user may identify 2 conditions and a goal, prioritized as condition 1, condition 2, and goal 1. A product P1 may have score of A3B1C4 for condition 1, A2B0C3 for condition 2, and A4B3C1 for goal 1. this would yield an aggregate score string of

"A3B1C4A2B0C3A4B3C1"

Which can be alphanumerically sorted against similarly constructed score strings for other products and thereby determine a ranking for a given product against multiple prioritized conditions and goals. This, ranking for example, would be useful for multivitamin supplements.

Some embodiments may use other scoring approaches. For example, one embodiment may assign a numerical weight to each rating, such as A=5 points; B=3 points, and C=1 points, and weight each A rated ingredient in a product, for example based on its percentage weight content in the product as a whole or relative to the aggregate weight of all active ingredients in the product, and then sum all the A-rated ingredients. Algebraically, this would yield a quantitative score Si' as follows:

$$S_i' = At + Bu + Cv,$$

where subscript i denotes product i, t denotes the ratio of the aggregate weight of A-rated ingredients in the product i to the total weight of all active ingredients in the product; u denotes the ratio of the aggregate weight of B-rated ingredients in the product to all active ingredients in the product; and v denotes the ratio of the aggregate weight of B-rated ingredients in the product to all active ingredients in the product. This weighting would provide the advantage of ranking products that contained a greater percentage of important active ingredients higher than those that had a lower percentage. Some embodiments may replace weight and use a measure of purity. Execution continues at block 270.

Block 270 entails identifying product to address any depletions likely to be associated with the user, with a depletion defined as an actual or likely biological deficiency of the user resulting from use of one or more prescription or OTC medications, supplements, food, etc. In the exemplary embodiment, this entails searching a depletion database which associates prescription and OTC medications as well as supplements and products with common depletions. Once the depletions are identified, another search is executed to identify effective product for those depletions. These products include vitamins, minerals, supplements and/or foods. Execution continues at block 280.

Block 280 entails outputting a set of one or more ranked products for each condition, goal, and depletions. In the exemplary embodiment, this entails outputting a webpage to an access device, such as access device 130 in FIG. 1. In some embodiments, for example those that provide for automatic update of user profiles based on medical examination events or biometric monitoring, the system is configured to deliver recommendations in any machine readable format including PDF, Microsoft Word, Microsoft Excel, text, email or alternately in the mail.

Block 290 entails processing a user purchase of one or more of the products selected from the results output in F Exemplary Graphical User Interface(s)

Figure 3A:
Figure 3B:
Figure 3C:

FIGS. 3A-3H show various portions, pages or screen shots, of an exemplary tabbed questionnaire 300, which serves as part of GUI 138 in FIG. 1. FIG. 3A shows a registration interface 310 for collecting basic user information, such as name email, user name, and password. FIG. 3B shows, a gender interface 320 for the user to provide gender information, as male or female. FIG. 3C shows an age interface 330 for use in collecting age information, for example in an age cohort designation or selection. Some embodiments allow users to simply enter a birthdate or current age.

Figure 3D:
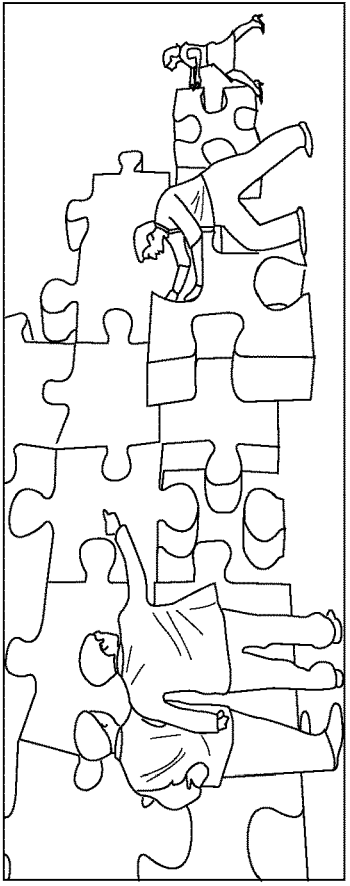

FIG. 3D shows a goals interface 340, via which invites the user to indicate one or more common wellness goals via selection of radio button. Exemplary fitness or wellness goals include: Better Skin Tone; Build Muscle, Compete, Disease Management, Flexibility, Gain Weight, Grow Hair, Have More Energy, Healthier Diet, Heart Health, Improve Posture, Improve Agility, Improve Arthritis, Improve Balance, Improve Circulation, Improve for a sport, Improve Memory, Improve Speed, Live Healthier, Loose Weight, Lose Fat, Muscle Definition, Stamina, Stronger Bones, Transform My Body, Increase Energy Level, Promote Longevity, Reduce Cancer Risk, Reduce Blood Pressure. In addition to the radio buttons, the user may use either drop-down menus of all wellness goals or an alpha-numeric search dialog box Some embodiments include an autocomplete or autosuggestion feature to help users identify and enter relevant conditions and/or other responses elsewhere in building the user profile.

Figure 3E:

FIG. 3E shows a medical conditions interface 350 which guides users to select or indicate one or more common medical conditions that he or she may have had or currently be experiencing: Exemplary medical conditions include: Age-related Cognitive Disorder, Alcoholism, Allergy, Angina, Anxiety, Arthritis, Asthma, Bronchitis, Cancer, Chronic Pain, Congestive Heart Failure (CHF), Depression, Diabetes, Erectile Dysfunction, Glaucoma, Gout, Headaches, Heart Disease, High Cholesterol, Hypertension, Indigestion, Insomnia, Jaundice, Kidney/bladder, Liver, Menopause, Obesity, Recurring Pain, Shortness of breath, Sexually Transmitted Diseases (STD), Stomach/Intestine, Stress, Stroke, Thyroid Trouble, Tuberculosis, Ulcer, Ulcers, Urinary Tract Infections. In addition to the radio buttons, the user may use either drop-down menus of all medical conditions or an alpha-numeric search dialog box Some embodiments include an autocomplete or autosuggestion feature to help users identify and enter relevant conditions and/or other responses elsewhere in building the user profile.

Some embodiments may ask the consumer to identify if close family members, for example parents or siblings have had any of these conditions and make recommendations assuming that the user has the condition.

FIG. 3F shows a biometric data interface 360. Interface 360 accepts input for one or more items of biometric information. Exemplary biometric information includes: RM Chest Press; activity level, Aerobic Test; Blood Pressure (Systolic/Diastolic); BMI (body mass index), Body Fat %, Body Weight, Cholesterol, Cholesterol/HDL Ratio, Dips, HDL, LDL, Oxygen Consumption (Vo2), Pull Ups, Push Ups, Resting Heart Rate, Sit and Reach, Sit Ups, Triglycerides, Waist/Hip Ratio. In some embodiments, interface 360 includes inputs or prompts enabling a user to subscribe or enroll in a biometric monitoring program that would allow for pushing or pulling of biometric data from a biometric monitoring service that the user is associated with and/or with one or more biometric monitoring devices that the user may regularly wear or have implanted in his or her body. In some instances, the user may provide access credentials and permissions for the system to access a third-party biometric monitoring system and/or his or her electronic medical records so that new medical or biometric conditions are brought into the system for use in making appropriate product recommendations.

Figure 3G:
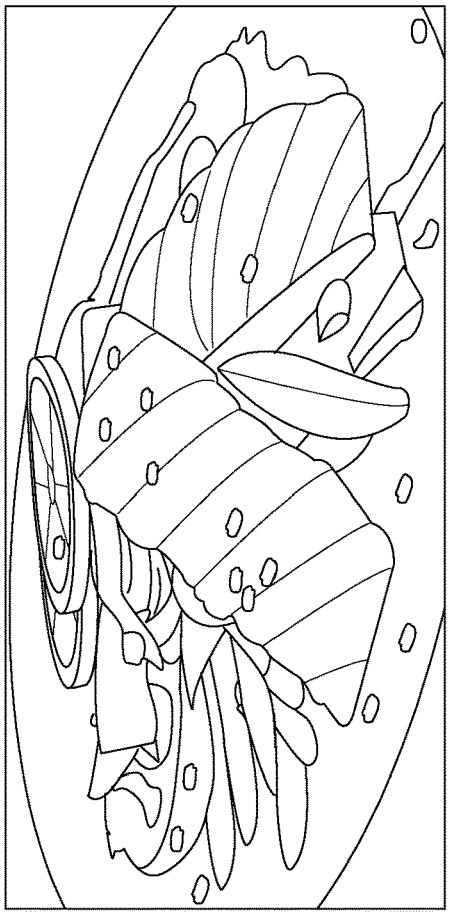

FIG. 3G shows a nutritional information interface 370, which presents one or more nutritional related questions or queries for user response. Exemplary questions include: Are you currently being treated for a medical condition; are you currently on a special (vegetarian, low-fat, gluten free) diet; are you taking any medications; are you taking any vitamin or nutritional supplements; do you drink alcoholic beverages; do you drink caffeine; do you eat breakfast; do you eat meal replacements or drink supplements; do you eat wheat products; do you have a family history of diabetes, high blood pressure, or high cholesterol; do you have food allergies In some embodiments, the user may provide permission and access credentials for online nutritional and/or physical activity diaries that provide the system information on the user habits and thereby enable more accurate recommendations. Physical activity data, for example, could be collected and provided by a fitness club where users exercised regularly. Still other embodiments may estimate nutritional or physical activity information from status updates provided on a social media service such as Facebook or Twitter, assuming that users would provide permissions and credentials for such access.

FIG. 3H shows an exemplary medical questionnaire interface 380. Exemplary medical questions or prompts include:

List the prescriptions and over-the-counter medications and dosages you are currently using; has your doctor ever said that you have a heart condition and that you should only do physical activity recommended by a doctor; do you feel pain in your chest when you do physical activity; in the past month, have you had chest pain when you were not doing physical activity; do you lose your balance because of dizziness or do you ever lose consciousness; Do you have a bone or joint problem (for example, back, knee or hip) that could be made worse by a change in your physical activity; Is your doctor currently prescribing drugs (for example, water pills) for your blood pressure or heart condition; do you know of any other reason why you should not do physical activity; have you had a physical exam with a physician in the past 2 year; have you ever had any of the following: Allergies, Anemia, Angina; are you 20 pounds overweight; Asthma, Blood Clots; Cancer, Cardiovascular Surgery; Coronary Artery Disease; Currently Pregnant, Emphysema; Heart Attack; Heart Valve Problem; Inflammation of a Vein; Osteoporosis; Pulmonary Disease; Rheumatic Fever; Stroke; Do you have any Major Risk Factors: Are you a Male over the age of 45 or a Woman over the age of 55; Do you currently smoke: Do you have cholesterol over 200 ml/dl; has your Father or Brother experienced a heart attack before age 55; Has your Doctor ever told you that you might have diabetes; Has your Doctor ever told you that you might have high blood pressure; has your Mother or Sister experienced a heart attack before age 65; Do you have any Major Signs or Symptoms Suggesting Cardiovascular and Pulmonary Disease: Pain or discomfort in the chest, neck, jaw, arms or other areas upon exertion; Shortness of Breath at rest or with mild exertion; Dizziness at rest or with mild exertion; Excessive accumulation of tissue fluid; Sudden rapid heart beats; Severe pain in your legs at rest or with mild exertion; abnormal heart rhythms; Unusual fatigue or shortness of breath with usual activities. The exemplary embodiment also includes a set of one or more Women-Only Questions including: Please list all your medical Exams; and Do you use Birth Control pills; Do you have any of the following: Abdominal pain; Anxiety; Bruising; Date of last physical; Depression; Digestive Tract; Fevers or night sweats; Food allergy; Food intolerance; Unhappiness; Have you ever been denied life insurance; Have you ever been hospitalized; Have you ever been treated for a nervous condition; Have you ever had surgery or been advised to do so; Hazardous Activities; How many hours of sleep do you get per night on average; Inability to assume certain positions; Inability to perform certain motions; Jaundice; Job Satisfaction; Seatbelt Usage; Marital Status; Nausea/vomiting; Rashes; Recent weight loss or gain; Recurrent infections; Relaxation; Sexual Disorders. Additional questions or prompts in the exemplary embodiment include: Tell us about your parents and grandparents longevity; What is your education; What is your Ethnicity?

Figure 4:
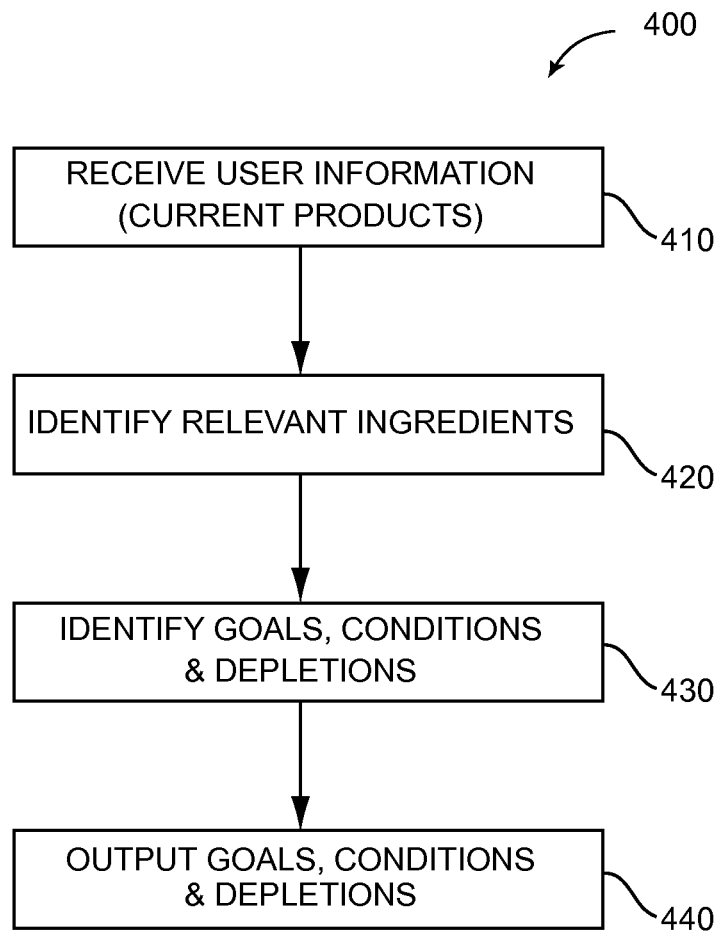
FIG. 4 is a flow chart of an exemplary method that corresponds to one or more embodiments of the present invention.
Figure 5:
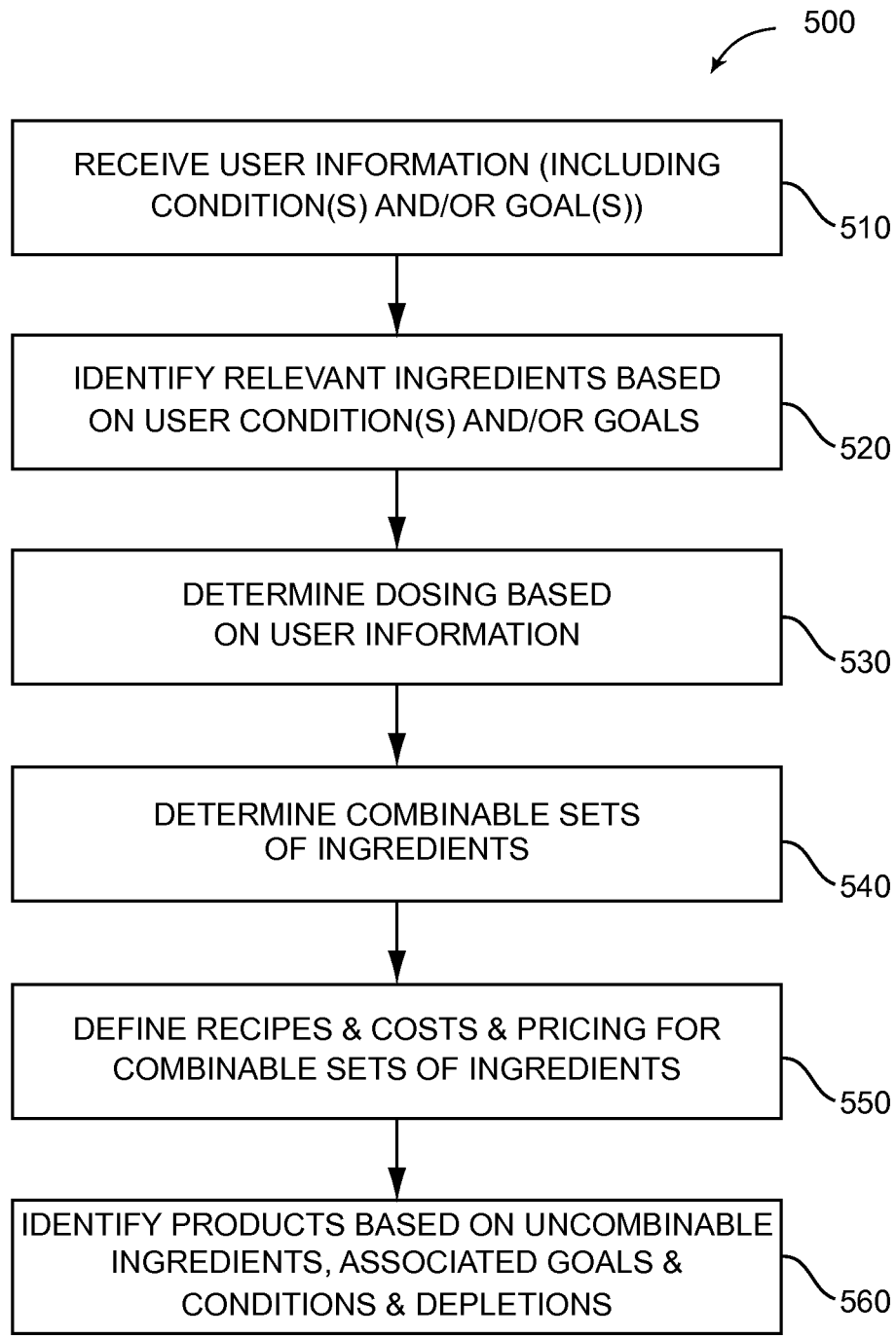
FIG. 5 is flow chart of an exemplary method that corresponds to one or more embodiments of the present invention.

FIG. 3I shows an exemplary results page 380, with a set of recommended products 391-393, each displayed in association with a selectable ratings indicator 391A-393A. Selection of a ratings indicator such as indicator 391A Additional Exemplary Methods FIG. 4 shows an alternative method of operating system 100, including process blocks 410 through 450. In Block 410, the system receives user information (current products, prescription medications, vitamins, minerals, supplement and foods); In Block 420, the system identifies relevant ingredients; in Block 430, the system identifies goals, conditions and depletions; in Block 440, the system outputs goals, conditions and depletions for each ingredient; in Block 450, the system outputs goals, conditions and depletions for current products, prescription medications, vitamins, minerals, supplements and foods FIG. 5 shows an alternative method 500 of operating system 100, including process blocks 510 through 560. In Block 510, the system receives user information (including goal(s) and/or condition(s); in Block 520, the system identifies relevant ingredients based on user goals(s) and/or condition(s); in Block 530, the system determines dosing based on user information; in Block 540, the system determines combinable sets of ingredients. To determine a combinable set of ingredients, the exemplary system includes a database of commonplace ingredients and which ingredients they're compatible with. The system then searches for an optimal set of binders based on the ingredients; in Block 550, the system defines recipes for combinable sets of ingredients; in Block 555, the system defines pricing for the combinable sets of ingredients; in Block 560, the system identifies products based upon combinable ingredients, associated goals, conditions and depletions; in Block 570, the system output product recommendations showing goals, conditions, depletions and relative efficacy ratings, sorted by descending efficacy; in Block 580, the system provides products to be purchased.

CONCLUSION

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

It will be appreciated that some embodiments may comprise one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, some embodiments can be implemented as a computer-readable storage medium (more generally a non-transient storage medium) having computer readable code stored thereon for programming a computer (e.g., comprising a processor) to perform a method as described and claimed herein. Likewise, computer-readable storage medium can comprise a non-transitory machine readable storage device, having stored thereon a computer program that include a plurality of code sections for performing operations, steps or a set of instructions.

Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

The claimed invention is:

1. An improved system for computerized finding and purchasing of user suitable wellness related products, the improved system comprising:
 a server including a processor and a memory and configured to provide a graphical user interface on a display device associated with a user, the graphical user interface having one or more input regions configured to receive user input identifying one or more medical conditions or wellness goals and user input indicating a submission command;
 an ingredients database having memory storing a set of two or more ingredient data structures, with each ingredient data structure including:
  an ingredient identifier for an ingestible ingredient in logical association with one or more medical conditions or wellness goals for which the ingredient has been independently scientifically demonstrated in published scientific articles to be effective and in logical association with depletion data identifying at least one substance prone to depletion upon ingestion of the ingredient by a human, and wherein each associated medical condition or wellness goal is further logically associated with an efficacy rating of the ingredient for the associated condition or goal based on at least one published scientific article and an effective dosage indicator indicating the dosage of the ingredient used to achieve the efficacy rating for the associated condition or goal;
 a products database having memory storing a set of two or more product data structures, with each product data structure including a product identifier for a wellness product in logical association with a Universal Product Code (UPC) and in logical association with one or more ingredient identifiers for ingredients contained within the product and corresponding ingredient quantity data indicating quantity of the associated ingredient in a portion of the product;
 a recommendations module responsive to one or more of the user input medical conditions or wellness goals and the user submission command to:
  automatically search the stored ingredient data structures of the ingredients database to identify two or more sets of found ingredients, with first and second ones of the sets of found ingredients each identifying two or more ingredients effective to at least a predetermined threshold level in addressing at least respective first and second ones of the medical conditions and wellness goals based on the efficacy ratings in their corresponding ingredient data structures increa;
  automatically search the stored product data structures of the products database, based on each of the found ingredients in each of the two or more sets of found ingredients, to identity one or more found product identifiers associated with each of the found ingredients or known equivalents to the found ingredients in their corresponding product data structures; and
  automatically determine an objective product efficacy score of each found product based at least on a count of found ingredients it includes and the efficacy rating of each found ingredient it includes;
  automatically sort two or more of the found product identifiers in objective rank order based on their corresponding objective product efficacy scores, with each of the two or more sorted found product identifiers having a respective objective product efficacy rank;
 an ecommerce module responsive to the recommendations module sorting of the two or more found product identifiers to cause display, as part of the graphical user interface associated with the user, of product information associated with one or more of the found product identifiers, an objective product efficacy rank indicator based on its product efficacy rank, and at least one user selectable feature for initiating an ecommerce purchase of one or more products corresponding to the one or more selected found product identifiers based on one or more UPC codes stored in the product data structures respectively associated therewith, thereby enabling the user to consider, select, and purchase one or more relevant wellness products based on an independent assessment of their efficacy for the user input goals and conditions.

2. The system of claim 1, wherein the recommendations module is configured to calculate a recommended dosage for each of the found ingredients based user-profile information received from the user via the graphical user interface and wherein the recommendations module is further responsive to each calculated recommended dosage to exclude one or more of product identifiers from being identified as a found product identifier.

3. The system of claim 2 wherein the user-profile information comprises at least one of prescription medication, over-the-counter medication, age, weight, gender, blood type, allergies, sensitivities, nutrition data, food products, ingestible chemical compounds, clubs, group associations, and other biometric markers.

4. The system of claim 3 wherein the recommendations module automatically excludes one or more products from being identified as found product identifiers when contraindicated by one or more portion of the user profile information.

5. The system of claim 4 wherein the recommendations module excludes a combination of selected products which result in contraindications amongst ingredients embedded therein.

6. The system of claim 1, wherein the objective product efficacy score of each found product is also based on a respective priority associated with each of the goals or conditions its corresponding found ingredients are effective.

7. The system of claim 1 wherein the recommendations module determines a count of the one or more ingredients within respective ones of the identified products having high efficacy rating, medium efficacy rating, and low efficacy rating.

8. The system of claim 7 wherein the recommendations module ranks a first product higher than a second product where the first product includes a greater number of high efficacy rated ingredients than a second product and the second product includes a greater number of at least one of medium and low efficacy rated ingredients than the first product.

9. The system of claim 1, further comprising a medications database communicatively coupled to the recommendations module wherein the medications database comprises prescription and over-the-counter medications.

10. The system of claim 9, further comprising one or more medication data structures associated with respective ones of the prescription and over-the-counter medications, each of the one or more medication data structures have respective contraindication and depletion fields associated therewith, wherein the contraindication field is configured to receive one or more ingredients, medications, and over-the-counter medications determined to be incompatible with the associated medication, and wherein the depletion field is configured to indicate a substance depleted from a user's body in response to ingesting the associated medication.

11. The system of claim 1 wherein the stored ingredients comprise chemical compounds.

12. The system of claim 6, wherein the ecommerce module is further responsive to the recommendation selection of the one or more product identifiers to cause presentation of the product efficacy score of each respective found one of the one or more products using a descending set of sequential efficacy grades A, B, C, D, F, or X, which are respectively defined as:

A=Strong Scientific Evidence: Statistically significant evidence of benefit from more than two properly randomized clinical trials (RCTs), OR evidence from one properly conducted RCT AND one properly conducted meta-analysis, OR evidence from multiple RCTs with a majority of the properly conducted trials showing statistically significant evidence of benefit AND with supporting evidence in basic science, animal studies, or theory;

B=Good Scientific Evidence: Statistically significant evidence of benefit from 1-2 properly randomized trials, OR evidence of benefit from more than one properly conducted meta-analysis OR evidence of benefit from more than one cohort/case-control/non-randomized trials AND with supporting evidence in science;

C=Unclear or Conflicting Scientific Evidence: Evidence of benefit from more than one small RCT(s) without adequate size, power, statistical significance, or quality of design by objective criteria, OR conflicting evidence from multiple RCTs without at least a majority of the properly conducted trials showing evidence of benefit or ineffectiveness, OR evidence of benefit from more than one cohort/case-control/non-randomized trials AND without supporting evidence in basic science, animal studies, or theory, OR evidence of efficacy only from basic science, animal studies, or theory;

D=Fair or Negative Scientific Evidence: Statistically significant negative evidence (i.e., lack of evidence of benefit) from cohort/case-control/non-randomized trials, AND evidence in science suggesting a lack of benefit;

F=Strong Negative Scientific Evidence: Statistically significant negative evidence (i.e., lack of evidence of benefit) from more than one properly randomized adequately powered trial(s) of high-quality design by objective criteria;

X=Unable to evaluate efficacy due to lack of adequate available human data.

* * * * *